United States Patent [19]

Bey et al.

[11] 4,438,270

[45] Mar. 20, 1984

[54] α-HALOMETHYL DERIVATIVES OF α-AMINO ACIDS

[75] Inventors: Philippe Bey, Strasbourg; Michel Jung, Illkirch-Graffenstaden, both of France

[73] Assignee: Merrell Toraude et Compagnie, Strasbourg, France

[21] Appl. No.: 392,051

[22] Filed: Jun. 25, 1982

Related U.S. Application Data

[63] Continuation of Ser. No. 53,937, Jul. 2, 1979, abandoned, which is a continuation of Ser. No. 814,765, Jul. 11, 1977, abandoned.

[51] Int. Cl.³ .................. C07D 211/76; C07D 223/10
[52] U.S. Cl. .............................. 546/243; 260/112.5 R; 260/239.3 R; 424/177; 424/244; 424/253; 424/267; 424/300; 424/309; 424/311; 424/313; 424/319; 424/320; 544/277; 560/16; 560/29; 560/30; 560/38; 560/39; 560/41; 560/147; 560/153; 560/159; 560/168; 560/169; 562/426; 562/444; 562/449; 562/556; 564/157; 562/560; 564/162; 564/164; 562/561; 564/165; 564/193; 564/154; 564/155
[58] Field of Search .................. 260/239.3 R; 546/243

[56] References Cited

U.S. PATENT DOCUMENTS 4,325,961 4/1982 Kollonitsch et al. ............ 424/273 R Primary Examiner—Richard Raymond
Attorney, Agent, or Firm—William J. Stein; Raymond A. McDonald; Gary D. Street

[57] ABSTRACT

Novel halomethyl derivatives of α-amino acids of the following general structure:

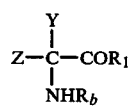

wherein Y is ClCH$_2$, F$_2$CH—, F$_3$C—, ClCH$_2$—, Cl$_2$CH—; Z is β-methylthioethyl, β-thioethyl, β-benzylthioethyl; S-(5′-desoxyadenosin-5′-yl)-S-methylthioethyl, γ-guanidinopropyl, R$_a$HN(CH$_2$)$_n$— wherein n is the integer 3 or 4 or

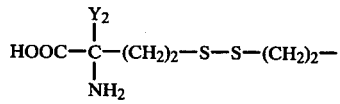

wherein Y$_2$ is F$_2$CH—, or F$_3$C—; each of R$_a$ and R$_b$ can be the same or different and is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

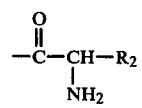

wherein R$_2$ is hydrogen, a straight or branched lower alkyl group of from 1 to 4 carbon atoms, benzyl or p-hydroxybenzyl; R$_1$ is hydroxy, a straight or branched alkoxy group of from 1 to 8 carbon atoms, —NR$_4$R$_5$ wherein each of R$_4$ and R$_5$ is hydrogen or a lower alkyl group of from 1 to 4 carbon atoms, or

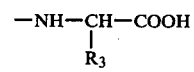

wherein R$_3$ is hydrogen, a straight or branched lower alkyl group of from 1 to 4 carbon atoms, benzyl or p-hydroxybenzyl; and the lactams thereof when Z is R$_a$HN(CH$_2$)$_n$— and each of R$_a$ and R$_b$ is hydrogen; with the provisos that when Z is γ-guanidinopropyl or β-methylthioethyl, Y is FCH$_2$—, F$_2$CH— or F$_3$C—; when Z is γ-guanidinopropyl, R$_1$ is hydroxy; and when Z is β-thioethyl, β-benzylthioethyl, S-(5′-desoxyadenosin-5′-yl)-S-methylthioethyl or 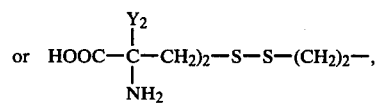

Y and Y$_2$ are FCH$_2$—, F$_2$CH—, or F$_3$C— and are the same, each of R$_a$ and R$_b$ is hydrogen and R$_1$ is hydroxy; and pharmaceutically acceptable salts and individual optical isomers thereof.

4 Claims, No Drawings

α-HALOMETHYL DERIVATIVES OF α-AMINO ACIDS

This is a continuation of application Ser. No. 053,937, filed July 2, 1979, now abandoned, which in turn is a continuation of Ser. No. 814,765, filed July 11, 1977, now abandoned.

FIELD OF INVENTION

This invention relates to novel and useful halomethyl derivatives of α-amino acids.

SUMMARY OF INVENTION

The compounds of the present invention may be represented by the following general Formula I:

Formula I

In the above general Formula I Y is $F_2CH-$, $F_3C-$, or $Cl_2CH-$; Z is β-methylthioethyl, β-thioethyl, β-benzylthioethyl, S-(5'-desoxyadenosin-5'-yl)-β-methylthioethyl, γ-guanidinopropyl, or $R_aHN(CH_2)_n-$ wherein n is the integer 3 or 4 or

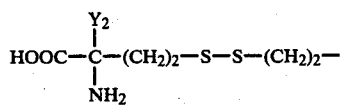

wherein $Y_2$ is $F_2CH-$, or $F_3C$; each of $R_a$ and $R_b$ is the same or different and is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the group

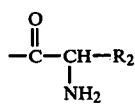

wherein $R_2$ is hydrogen, a straight or branched lower alkyl group of from 1 to 4 carbon atoms, benzyl or p-hydroxybenzyl; and $R_1$ is hydroxy, a straight or branched alkoxy group of from 1 to 8 carbon atoms, $-NR_4R_5$ wherein each $R_4$ and $R_5$ is hydrogen or a lower alkyl group of from 1 to 4 carbon atoms, or the group

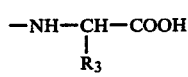

wherein $R_3$ is hydrogen, a straight or branched lower alkyl group of from 1 to 4 carbon atoms, benzyl or p-hydroxybenzyl; with the provisos that when Z is γ-guanidinopropyl or β-methylthioethyl, Y is $F_2CH-$, or $F_3C-$, when Z is γ-guanidinopropyl $R_1$ is hydroxy; and when Z is β-thioethyl, β-benzylthioethyl, S-(5'-desoxyadenosin-5'-yl)-S-methylthioethyl or

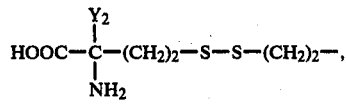

Y and $Y_2$ are $F_2CH-$, or $F_3C-$ and are the same, each of $R_a$ and $R_b$ is hydrogen and $R_1$ is hydroxy. The lactams of the compounds of general Formula I wherein Z is $R_aHN(CH_2)_n-$ and each of $R_a$ and $R_b$ is hydrogen are also within the scope of the present invention. Pharmaceutically acceptable salts and individual optical isomers of the compounds of general Formula I are also included within the scope of the present invention.

DETAILED DESCRIPTION OF INVENTION

In the above general Formula I in addition to the group $R_aHN(CH_2)_n-$ and

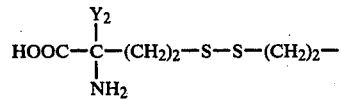

the symbol Z represents the substituent groups β-methylthioethyl, β-thioethyl, β-benzylthioethyl, S-(5'-desoxyadenosin-5'-yl)-β-methylthioethyl and γ-guanidinopropyl which are depicted by the following structures:

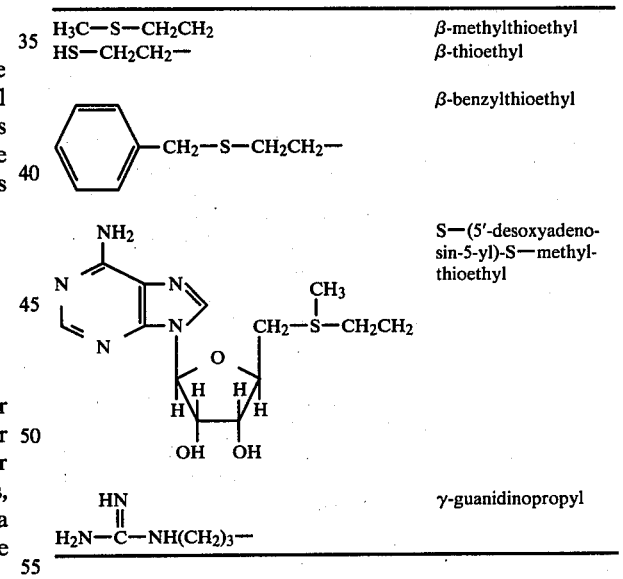

As used in general Formula I the term alkylcarbonyl is taken to mean the group

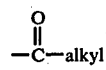

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

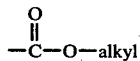

wherein the alkoxy moiety, that is, —O—alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, propoxy, butoxy, pentyloxy, and octyloxy.

The lactams of the compounds of general Formula I wherein Z is $R_aHN(CH_2)_n$—, and each of $R_a$ and $R_b$ is hydrogen are represented by the following general Formula II:

In the above general Formula II, n is the integer 3 or 4, and Y is $F_2CH$—, $F_3C$—, or $Cl_2CH$—.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric, cyclamic and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of this invention are those of general Formula I wherein $R_1$ is hydroxy. More preferred compounds of this invention are those of general Formula I wherein $R_1$ is hydroxy, Z is β-methylthioethyl, S-(5'-desoxyadenosin-5'-yl)-S-methylthioethyl, γ-guanidinopropyl or $R_aHN(CH_2)_n$— and each of $R_a$ and $R_b$ is hydrogen and the lactams of said compounds wherein Z is $R_aHN(CH_2)_n$—. Another preferred embodiment of this invention is the compounds of general Formula I and the lactams thereof wherein Y is other than $F_3C$— with compounds wherein Y is $F_2CH$— being more preferred.

Illustrative examples of compounds of the present invention are the following:
2-amino-2-difluoromethyl-4-methylthiobutyric acid,
2-amino-2-trifluoromethyl-4-[S-(5'-desoxyadenosin-5=-yl)-S-(methyl)thio]butyric acid,
2-amino-2-difluoromethyl-4-thiobutyric acid,
2-dichloromethyl-2,5-diaminovaleric acid,
2-dichloromethyl-2,6-diaminocaproic acid,
methyl 2-amino-2-difluoromethyl-4-methylthiobutyrate,
2-amino-2-trifluoromethyl-4-methylthiobutyric acid,
2-amino-2-difluoromethyl-4-[S-(5'-desoxyadenosin-5'-yl)-S-(methyl)thio]butyric acid,
2-amino-2-difluoromethyl-5-guanidinovaleric acid,
2-amino-2-trifluoromethyl-5-guanidinovaleric acid,
2,5-diamino-2-difluoromethylvaleric acid,
2,5-diamino-2-trifluoromethylvaleric acid,
2,6-diamino-2-difluoromethylcaproic acid,
2,6-diamino-2-trifluoromethylcaproic acid,
2-amino-4-benzylthio-2-difluoromethylbutyric acid,
2,9-diamino-2,9-difluoromethylhomocystine,
methyl 2-amino-2-difluoromethyl-4-[S-(5'-desoxyadenosin-5'-yl)-S-(methyl)thio]butyrate,
methyl 2,5-diamino-2-difluoromethylvalerate,
ethyl 2,5-diamino-2-dichloromethylvalerate,
n-propyl 2,5-diamino-2-trifluoromethylvalerate,
n-butyl 2,6-diamino-2-difluoromethylcaproate,
isopropyl 2-amino-2-difluoromethyl-4-methylthiobutyrate,
N,N-dimethyl 2,5-diamino-2-difluoromethylvaleramide,
pivalyl 2,6-diamino-2-trifluoromethylcaproate,
N-methyl 2-amino-2-difluoromethyl-4-methylthiobutyramide,
N-methyl 2-amino-2-trifluoromethyl-4-[S-(5'-desoxyadenosin-5'-yl)-S-(methyl)thio]butyramide,
N-ethyl 2-amino-2-difluoromethyl-5-guanidinovaleramide,
N-n-butyl 2,5-diamino-2-trifluoromethylvaleramide,
2-amino-2-trifluoromethyl-4-methylthio-1-oxobutylaminoacetic acid,
6-amino-2-dichloromethyl-2-(1-oxopropylamino)caproic acid,
2-difluoromethyl-4-[S-(5'-desoxyadenosin)5'-yl)-S-(methyl)-thio]-2-(1-oxoethylamino)butyric acid,
N-methyl 2-dichloromethyl-2,5-di-(1-oxoethylamino)valeramide, and methyl 2-difluoromethyl-2,5-di-(2-amino-1-oxoethylamino)caproate.

The compounds of general Formula I have many utilities. The compound of general Formula I wherein Z is β-thioethyl, β-benzylthioethyl or

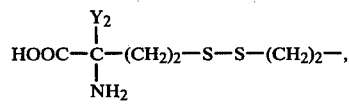

each of $R_a$ and $R_b$ is hydrogen and $R_1$ is hydroxy are useful as intermediates in the preparation of the corresponding pharmaceutically useful compound wherein Z is S-(5'-desoxyadenosin-5'-yl)-S-methylthioethyl.

The compounds of general Formulas I and II wherein Z is other than β-thioethyl, β-benzylthioethyl or

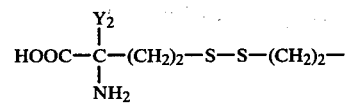

are inhibitors of decarboxylase enzymes which are involved in polyamine formation rendering said compounds useful as pharmacological agents. Polyamines, particularly putrescine, spermidine and spermine are present in plant and animal tissues and in some microorganisms. Although the exact physiological role of polyamines has not been clearly delineated there is evidence to suggest that polyamines are involved with cell division and growth. (H. G. Williams-Ashman et al., The Italian J. Biochem. 25, 5–32 (1976), A. Raina and J. Janne, Med. Biol. 53, 121–147 (1975) and D. H. Russell, Life Sciences 13, 1635–1647 (1973)). Polyamines are essential growth factors for or involved in the growth processes of certain microorganisms, for example, *E. coli*, Enterobacter, Klebsiella, *Staphylococcus aureus*, *C. cadaveris*, *Salmonella typhosa* and *Haemophilus parainfluenza*. Polyamines are associated with both normal and neoplastic rapid growth there being an increase in the synthesis and accumulation of polyamines following a stimulus causing cellular proliferation. Also, levels of polyamines are known to be high in embryonic systems, the tests, in patients with rapidly growing tissues. It is known that there is a correlation between the activity of the decarboxylase enzymes of ornithine, S-adenosylmethionine, arginine and lysine and polyamine formation.

The biosyntheses of putrescine, spermidine and spermine are interrelated. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, after which the propylamine moiety of activated methionine may be transferred to putrescine to form spermidine or the polyamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosylmethionine decarboxylase and is known to be essential to growth processes of many microorganisms, for example, *H. parainfluenza*.

The compounds of general Formula I wherein Z is $R_aHN(CH_2)_n$— and the lactams thereof are inhibitors of ornithine decarboxylase and lysine decarboxylase respectively as n varies from 3 to 4. The compounds of general Formula I wherein Z is β-methylthioethyl or S-(5'-desoxyadenosin)5'-yl)-β-methylthioethyl are inhibitors of S-adenosylmethionine decarboxylase and wherein Z is γ-guanidinopropyl are inhibitors of arginine decarboxylase. As inhibitors of the above-enumerated decarboxylase enzymes the compounds of general Formulas I and II wherein Z is other than β-thioethyl, β-benzylthioethyl or

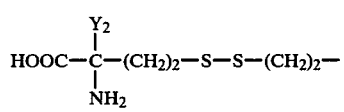

are useful as antiinfective agents being effective in the control of microorganisms, for example, bacteria and viruses which are dependent upon polyamines for growth, for example, *E. coli*, Enterobacter, Klebsiella, *Staphylococcus aureus*, *C. cadaveris*, viruses such as, *H. parainfluenza*, picornaviruses, for example, encephalomyocarditis, *Herpes simplex*, poxviruses and arboviruses, for example *Semliki forest*. The compounds of general Formulas I and II wherein Z is other than β-thioethyl, β-benzylthioethyl,

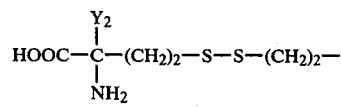

and $R_aHN(CH_2)_4$— are also useful in the control of certain rapid growth processes. For example, the compounds are useful in the inhibition of spermatogenesis and embryogenesis and therefore the compounds find use as male antifertility agents and abortifacients. The compounds are also useful in the inhibition of the immune response, thus the compounds are useful as immunosuppressants, and are useful in the control of neoplastic growth, for example, solid tumors, leukemias and lymphomas.

The compounds are also useful as inhibitors of prostatic hypertrophy, excessive scalp cell growth as found with the occurrence of dandruff and as inhibitors of abnormal cutaneous cell growth as found with a psoriatic condition. The utility of compounds of general Formula I wherein Z is other than β-thioethyl, β-benzylthioethyl or

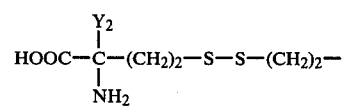

as irreversible inhibitors of ornithine or S-adenosylmethionine decarboxylase enzymes in vivo can be demonstrated as follows. An aqueous solution of an appropriate compound of Formula I is given orally or parenterally to male mice or rats. The animals are sacrificed 1 to 48 hours after administration of the compound, and the ventral lobes of the prostate removed and homogenized with the activity of ornithine or S-adenosylmethionine decarboxylase enzyme being measured as generally described by E. A. Pegg and H. G. Williams-Ashman, Biochem. J. 108, 533–539 (1968) and J. Janne and H. G. Williams-Ashman, Biochem. and Biophys. Res. Comm. 42, 222–228 (1971).

The compounds of general Formula I wherein $R_1$ is hydroxy and Z is other than

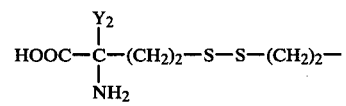

are useful as chemical intermediates for the preparation of novel cephalosporin derivatives which are useful as antibiotics and have the following general structure:

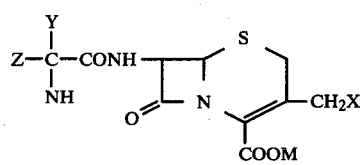

Formula III wherein Z and Y have the meanings defined in general Formula I except Z is not

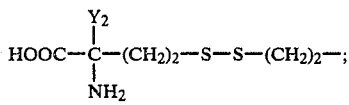

M is hydrogen or a negative charge; and X is hydrogen or acetoxy.

The compounds of general Formula III and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate; fumarate, malate and ascorbate. The salts can be formed by conventional means.

Illustrative examples of compounds of general Formula III are 7-[[2,5-diamino-2-difluoromethylvaleryl]amino]-3-acetyloxymethyl-8-oxo-5-thia-1-azabicyclo[4.2.0]oct-2-ene-2-carboxylic acid, and 7-[[2-amino-2-trifluoromethyl-δ-guanidinovaleryl]amino]-3-acetyloxymethyl-8-oxo-5-thia-1-azabicyclo[4.2.0]oct-2-ene-2-carboxylic acid.

The preparation of the compounds of general Formula III is described hereinbelow.

As pharmacologically useful agents the compounds of general Formulas I and II can be administered in various manners to the patients being treated to achieve the desired effect. The compounds can be administered alone or in combination with one another. Also, the compounds can be administered in the form of a pharmaceutical preparation. The compounds may be administered orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 500 mg/kg of body weight of the patient per unit dose and preferably will be about 10 mg/kg to about 100 mg/kg of body weight of patient per unit dose. For example, a typical unit dosage form may be a tablet containing from 10 to 300 mg of a compound of Formulas I or II which may be administered to the patient being treated 1 to 4 times daily to achieve the desired effect.

As used herein the term patient is taken to mean warm blood animals such as mammals, for example, cats, dogs, rats, mice, guinea pigs, horses, bovine cows, sheep and humans.

The solid unit dosage forms can be of the conventional type. Thus, the solid form can be a capsule which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein Z is β-methylthioethyl, β-thioethyl or $R_aHN(CH_2)_n$—, $R_1$ is hydroxy and each of $R_a$ and $R_b$ is hydrogen are prepared by treating respectively an ester derivative of methionine homocysteine, ornithine or lysine wherein the amino group(s) is suitably protected and wherein the mercapto group of homocysteine is suitably protected with a strong base to form the carbanion intermediate which is reacted with a suitable halomethyl-halo alkylating reagent in an aprotic solvent, such as, dimethylsulfoxide, dimethylformamide, dimethylacetamide, benzene, toluene, ethers, such as, tetrahydrofuran, diethyl ether or dioxane and in the presence of hexamethylphosphortriamide when Y is other than $F_2CH$— at a temperature of about $-120°$ C. to $120°$ C., preferably about 25° to 50° C. for about ½ hour to 48 hours followed by acid or base hydrolysis as represented by the following reaction sequence.

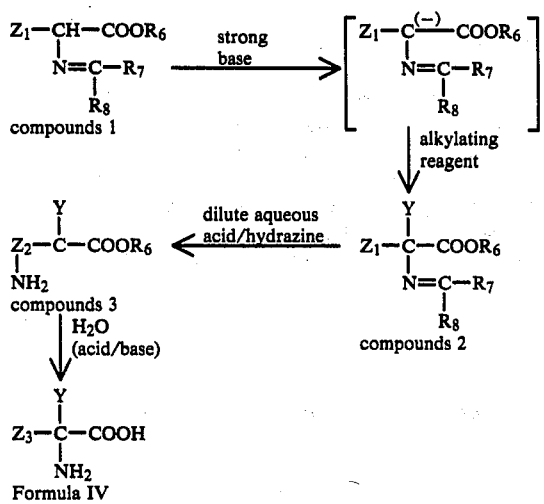

compounds 1 compounds 2 compounds 3

Formula IV

In the above reaction sequence $R_6$ is a lower alkyl group, for example, methyl, ethyl, isopropyl, n-propyl or n-butyl; $R_7$ is hydrogen, phenyl, a straight or branched alkyl group having from 1 to 8 carbon atoms, methoxy or ethoxy; $R_8$ is phenyl or a straight or branched alkyl group of from 1 to 8 carbon atoms; or $R_7$ and $R_8$ taken together may form an alkylene group of from 5 to 7 carbon atoms, that is, $-CH_2-(CH_2-)_m-CH_2-$ wherein m is an integer of from 3 to 5. Illustrative examples of straight or branched alkyl groups of from 1 to 8 carbon atoms which $R_7$ and $R_8$ may represent are, for example, methyl, ethyl, n-propyl, isopropyl, n-butyl, tert-butyl, n-pentyl, neopentyl or triethylmethyl; $Z_1$ is β-methylthioethyl; $R_9S(CH_2)_2-$ wherein $R_9$ is trityl, alkylcarbonyl wherein the alkyl moiety has from 1 to 4 carbon atoms and is straight or branched, such as, methyl, ethyl, or isopropyl, alkoxycarbonyl wherein the alkoxy moiety has from 1 to 4 carbon atoms and is straight or branched, such as, methoxy, ethoxy, isopropoxy, phenylcarbonyl or benzyloxycarbonyl; $R_{10}(CH_2)_n-$ wherein n is the integer 3 or 4 and $R_{10}$ is

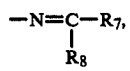

wherein $R_7$ and $R_8$ have the meanings defined above,

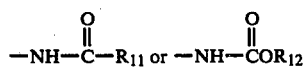

wherein each of $R_{11}$ and $R_{12}$ is phenyl, benzyl or a lower alkyl group of from 1 to 4 carbon atoms that is straight or branched, for example, methyl, ethyl or isopropyl; $Z_2$ is β-methylthioethyl, $R_9S(CH_2)_2-$ or $R_{13}(CH_2)_n-$ wherein $R_{13}$ is $-NH_2$,

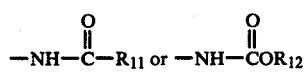

wherein $R_9$, $R_{11}$ and $R_{12}$ have the above defined meanings; $Z_3$ is β-methylthioethyl, β-thioethyl or $H_2N(CH_2)_n-$ wherein n is the integer 3 or 4; and Y has the meaning defined in Formula I with the proviso that when $Z_2$ is β-methylthioethyl or β-thioethyl Y is $F_2CH-$, or $F_3C-$. When in compounds 1 $Z_1$ is $R_{10}(CH_2)_n-$ wherein $R_{10}$ is

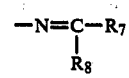

each $R_7$ and $R_8$ is the same.

Suitable strong bases which may be employed in the above reaction sequence to form the carbanion intermediate are those which will abstract a proton from the carbon atom alpha to the carboxy group, such as, alkyl lithium, for example, butyl lithium or phenyl lithium, lithium di-alkylamide, for example, lithium diisopropylamide, lithium amide, tertiary potassium butylate, sodium amide, metal hydrides, for example, sodium hydride or potassium hydride, tertiary amines, such as, triethylamine, lithium acetylide or dilithium acetylide. Lithium acetylide, dilithium acetylide, sodium hydride, and lithium diisopropylamide are particularly preferred bases.

Suitable alkylating reagents which may be employed in the above reaction sequence are illustratively chlorodifluoromethane, bromodifluoromethane, difluoroiodomethane, bromotrifluoromethane, chlorotrifluoromethane, trifluoroiodomethane, dichloromethane, bromodichloromethane and dichloroiodomethane. The alkylating reagents are known in the art.

Removal of the protecting groups of the amine, mercapto and carboxylic function may be achieved in one step by treatment of compounds 2 with aqueous acid, for example, hydrochloric acid or toluene sulfonic acid at a temperature of about 0° to 160° C. for about 4 to 24 hours to give compounds of general Formula IV. It is preferred to remove first the protecting groups of the amine function(s) of compounds 2 when said functions are protected as a Schiff's base by treating compounds 2 with dilute aqueous acid, for example, hydrochloric acid or with hydrazine or phenylhydrazine in solvents, such as, lower alcohols, for example, methanol or ethanol, ethers, chlorinated hydrocarbons, benzene and water. Removal of the protecting groups of the carboxylic functions, the mercapto group and the amine group(s) when the amine group(s) is protected other than as a Schiff's base is achieved by treatment of compounds 3 with concentrated aqueous acids, for example, hydrobromic acid at a temperature of about 0° to 160° C. or in aqueous bases, for example, ammonium hydroxide. Removal of the mercapto protecting group is carried out in the absence of oxygen, for example, under a nitrogen atmosphere.

The amine protected ester derivatives, that is, compounds 1 wherein $Z_1$ is β-methylthioethyl, $R_9S(CH_2)_2-$ or $R_{10}(CH_2)_n-$ wherein n, $R_9$ and $R_{10}$ have the meanings defined above are prepared, when $R_7$ is other tham methoxy or ethoxy, by treating an appropriate amino acid ester with a carbonyl bearing compound to form a Schiff's base in a generally known manner, specifically, (a) when $R_7$ is hydrogen, by treating the appropriate amino acid ester with benzaldehyde or an alkanal having from 1 to 9 carbon atoms being straight or branched, for example, 1-propanal, 1-butanal, 2,2-dimethylpropan-1-al or 2,2-diethylbutan-1-al; (b) when $R_7$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_7$ is a straight or branched alkyl group having from 1 to 8 carbon atoms, treating the appropriate amino acid ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When $R_7$ is methoxy or ethoxy, an appropriate amino acid ester derivative is reacted with benzoyl halide, for example, chloride or an alkanoic acid halide, for example, chloride wherein the alkanoic acid has from 1 to 9 carbon atoms and may be straight or branched, such as, acetyl chloride, propionyl chloride, butyryl chloride, tert-butyryl chloride, 2,2-diethylbutyric acid chloride or valeryl chloride, at 0° C. in ethers, methylenechloride, dimethylformamide, dimethylacetamide or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_7$ is methoxy or triethyloxonium tetrafluoroborate when $R_7$ is ethoxy at about 25° C. in a chlorinated hydrocarbon solvent such as methylene chloride, chlorobenzene or chloroform, and the reaction mixture is refluxed for about 12 to 20 hours. The mixture is then cooled to about 25° C. and an organic base such as triethylamine or pyridine is added after which the solution is extracted with brine and the product isolated.

When in compounds 1 $R_7$ and $R_8$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

When $Z_1$ is $R_9S(CH_2)_2$— in compounds 1 the mercapto protecting group is added to homocysteine in the absence of oxygen for example, under a nitrogen atmosphere by procedures generally known in the art, for example, L. Zervas and I. Photaki, J. Am. Chem. Soc. 84, 3887 (1962), L. Zervas, et al., J. Am. Chem. Soc. 85, 1337 (1963) and A. Berger, et al., J. Am. Chem. Soc. 78, 4483 (1956). Generally, when $R_9$ is trityl a slight excess of trityl chloride is added to homocysteine in a solvent such as dimethylformamide. When $R_9$ is alkylcarbonyl or phenylcarbonyl slightly less than 1 equivalent of an appropriate acid halide, for example, acetyl chloride, propionyl chloride or benzoyl chloride in an ether solvent, such as, tetrahydrofuran is added to 1 equivalent of homocysteine in an aqueous base, such as, aqueous sodium carbonate. Similarly when $R_9$ is alkoxycarbonyl or benzyloxycarbonyl slightly less than 1 equivalent of an appropriate alkyl haloformate such as methyl chloroformate or ethyl chloroformate or benzyl chloroformate in an ether solvent is added to 1 equivalent of homocysteine in aqueous base.

When $Z_1$ is $R_{10}(CH_2)_n$— wherein $R_{10}$ is

protecting groups are added to the corresponding free amino acids, that is, ornithine and lysine, by treatment of said amino acid with an excess of copper salt, for example, copper carbonate in boiling water for about 1 to 6 hours, and upon cooling to room temperature the insoluble materials are filtered off, and the filtrate is treated with an appropriate acid halide when $R_{10}$ is

or an appropriate alkyl or aryl haloformate when $R_{10}$ is

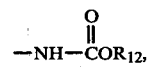

for example, in acetone in the presence of a base such as sodium bicarbonate or sodium hydroxide followed by treatment with hydrogen sulfide. Illustrative acid halides which may be employed are acetyl chloride, propionyl chloride, benzoyl chloride or 2-phenylacetyl chloride. Illustrative haloformates which may be employed are benzyl chloroformate, phenyl chloroformate, methyl chloroformate or ethyl chloroformate.

The amino acid ester is formed by generally known procedures, for example, the amino acid is treated with an appropriate alcohol, such as, methanol, ethanol, or n-butanol saturated with HCl gas.

The compounds of general Formula I wherein Z is γ-guanidinopropyl are prepared from the corresponding suitably protected derivative wherein Z is $R_aHN(CH_2)_n$— wherein $R_a$ is hydrogen and n is the integer 3 and wherein Y is $F_2CH$—, $F_3C$—, that is, the compound

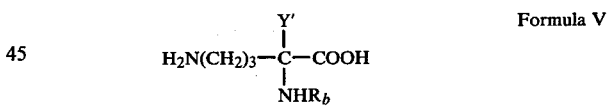

Formula V wherein Y' is $F_2CH$—, or $F_3C$— wherein $R_b$ has the meaning defined in Formula I by treatment with an alkylisothiouronium salt, for example, ethylisothiouronium hydrobromide by procedures generally known in the art, for example, *Organic Synthesis* III, p. 440 (1955). The reaction is carried out in the presence of a base, for example, aqueous sodium hydroxide or potassium hydroxide at a pH of about 8–12 and at a temperature of about 0° to 100° C. for about 6 hours to 8 days after which the reaction mixture is neutralized with concentrated mineral acid, for example, hydrochloric acid and the product isolated. When $R_b$ is hydrogen the α-amino group may be protected with, for example, a benzyloxycarbonyl group. When $R_b$ is

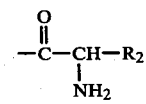

the free amino group is protected prior to the reaction with, for example, benzyloxycarbonyl. The amine protecting group is subsequently removed by acid hydrolysis, for example, with hydrochloric acid.

The compounds of general Formula I wherein Z is S-(5'-desoxyadenosin-5'-yl)-S-methylthioethyl are prepared by reacting 5'-p-toluenesulfonyl adenosine, 5'-chloroadenosine or 5'-bromoadenosine having the structure optionally protected as the 2',3'-isopropylidene

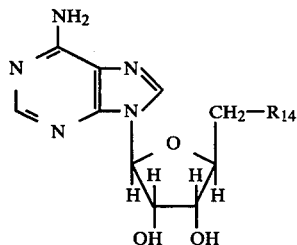

Formula VI wherein $R_{14}$ is p-toluenesulfonyl, chlorine or bromine with a metallic salt of an appropriate α-halomethylhomocysteine of the structure

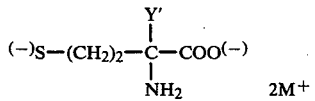

Formula VII wherein Y' is $F_2CH-$ or $F_3C-$ and $M^+$ is sodium or lithium in liquid ammonia for about 1 to 5 hours to form the S-adenosyl-α-halomethylhomocysteine derivative which is hydrolyzed with acid, such as, hydrochloric acid when the compound of Formula VI is protected as the 2',3'-isopropylidene then treated with methyl iodide in acidic solvents, such as, formic acid, acetic acid or mixtures thereof.

The metallic salts of the halomethylhomocysteine derivative, that is, the compounds of Formula VII are obtained by the addition of sodium or lithium metal to an appropriate α-halomethylhomocysteine, α-halomethylhomocystine or α-halomethyl-S-benzylhomocysteine wherein in each compound type the halomethyl group is $F_2CH-$ or $F_3C-$ in liquid ammonia until the blue color persists for 15 minutes.

The α-halomethyl-S-benzylhomocysteine derivatives are prepared by treating the corresponding α-halomethylmethionine, the synthesis of which is described hereinabove, with benzyl chloride by procedures generally known in the art, for example, Biochemical Preparations 5, 91 (1957). The reaction is carried out in concentrated hydrochloric acid at reflux temperature for about 24 hours after which the reaction mixture is concentrated under reduced pressure, neutralized with base, for example, ammonia and the product isolated. The α-halomethyl-S-homocystine derivatives are prepared by air oxidation of an aqueous solution of the corresponding halomethylhomocysteine at a pH of about 4 to 8 in the presence of a catalytic amount of a ferric salt, for example, ferric chloride.

Following is described the preparation of compounds of general Formula I wherein $R_a$ and/or $R_b$ are other than hydrogen including compounds of general Formula V. The following description is applicable to all the above said compounds, however, it is necessary to protect one or the other of the amino groups prior to treatment with the appropriate reactant, that is, acid halide or anhydride, alkyl haloformate or acid of the formula

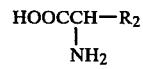

or anhydride thereof as described below to give compounds wherein either or both of $R_a$ and $R_b$ is other than hydrogen as follows: When $R_a$ is hydrogen and $R_b$ is other than hydrogen, the amino group to which $R_6$ is attached is protected as a copper salt by treatment of the corresponding derivative wherein $R_a$ and $R_b$ are hydrogen with an excess of a copper salt, for example, copper carbonate after which the amino group to which $R_a$ is attached is protected with, for example, benzyloxycarbonyl or tert-butoxycarbonyl by treatment with benzyl chloroformate or tert-butoxycarbonyl azide respectively followed by treatment with hydrogen sulfide, by procedures generally known in the art and illustrated more fully in the specific examples contained herein, prior to treatment with the appropriate reactant described below to give compounds wherein $R_b$ is other than hydrogen. The $R_a$ amine protecting group is subsequently removed by treatment with acid, for example, trifluoroacetic acid, HBr in dioxane or HBr in acetic acid or hydrogenolysis. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different or to give compounds of Formula I wherein Z is γ-guanidinopropyl as described hereinabove. In preparing compounds wherein $R_a$ is other than hydrogen and $R_b$ is hydrogen the amino group to which $R_b$ is attached is protected as a copper salt by treatment of the corresponding derivative wherein each $R_a$ and $R_b$ is hydrogen with an excess of copper salt, for example, copper carbonate prior to treatment with the appropriate reactant described below followed by acid or base hydrolysis and subsequently treating with hydrogen sulfide.

The compounds of general Formulas I and V wherein $R_a$ or $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or as to compounds of Formula I, $R_b$ is other than hydrogen as described above and $R_1$ is hydroxy with an acid halide of the formula

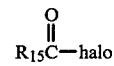

wherein halo is a halogen atom, for example, chlorine or bromine and $R_{15}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with acid or hydrogenolysis.

The compounds of general Formulas I and V wherein $R_a$ or $R_b$ is alkoxycarbonyl wherein the alkoxy moiety is straight or branched and has from 1 to 4 carbon atoms and $R_1$ is hydroxy are prepared by treating the corresponding derivative wherein $R_a$ and $R_b$ is hydrogen or is suitably protected or as to compounds of Formula I, $R_b$ is other than hydrogen as described hereinabove with an alkyl haloformate of the formula

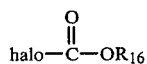

wherein halo is a halogen atom such as chlorine or bromine and $R_{16}$ is a straight or branched alkyl group having from 1 to 4 carbon atoms in water in the presence of a base such as sodium hydroxide or sodium borate at a temperature of about 0° to 25° C. for about ½ hour to 6 hours. When appropriate, protecting groups are removed as described hereinabove by treatment with acid or hydrogenolysis.

The compounds of general Formulas I and V wherein $R_a$ or $R_b$ is

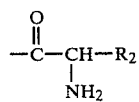

wherein $R_2$ is hydrogen, a straight or branched lower alkyl group of from 1 to 4 carbon atoms, benzyl or p-hydroxybenzyl and $R_1$ is hydroxy are prepared by treating the corresponding derivative wherein $R_a$ or $R_b$ is hydrogen or is suitably protected or as to compounds of Formula I, $R_b$ is other than hydrogen as described hereinbove with an acid of the formula

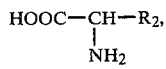

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate, hydrogenolysis to remove the protecting groups.

The compounds of the general Formula I wherein $R_1$ is a straight or branched alkoxy group of from 1 to 8 carbon atoms are prepared by converting the corresponding compound wherein $R_1$ is hydroxy to the acid halide by, for example, treatment with thionyl chloride, followed by alcoholysis with an alcohol of the formula $R_{17}OH$ wherein $R_{17}$ is a straight or branched alkyl group having from 1 to 8 carbon atoms by procedures generally known in the art. Alternatively, compounds of general Formula I wherein $R_1$ is a straight or branched alkoxy group of from 1 to 8 carbon atoms may be prepared from the corresponding derivative wherein $R_1$ is hydroxy by treatment of said derivative with an alcohol of the formula $R_{17}OH$ as defined above saturated with HCl for about 30 minutes for 12 hours at a temperature of about 25° C. to the boiling point of the alcohol.

The compounds of this invention wherein $R_1$ is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein $R_1$ is hydroxy and $R_a$ and $R_b$ have the meanings defined in general Formula I with the proviso that any free amino group is suitably protected with groups, such as, carbobenzyloxy or tert-butoxycarbonyl with an excess of an appropriate amine which may be represented as $HNR_4R_5$. The reaction is carried out in methylene chloride, chloroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine, or di-n-butylamine. Following the acylation reaction the protecting groups are removed by treatment with acid, for example, trifluoroacetic acid or hydrogen bromide in dioxane.

The compounds of general Formula I wherein $R_1$ is

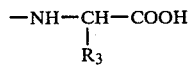

are prepared by reacting the corresponding derivative wherein $R_1$ is hydroxy or a functional derivative thereof, such as, an acid anhydride and $R_a$ and $R_b$ have the meanings defined in Formula I with the proviso that any free amino group is protected with a suitable blocking group, such as, benzyloxycarbonyl, tert-butoxycarbonyl by reacting the amine protected free acid with a compound of the structure

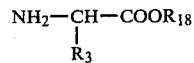

wherein $R_3$ has the meaning defined in general Formula I and $R_{18}$ is a lower alkyl group, for example, methyl or ethyl in an ether solution, such as, tetrahydrofuran or dioxane at about 0° C. to 35° C. for about 1 to 20 hours followed by acid then base hydrolysis, for example, with 2 N aqueous $NH_3$ at about 0° to 50° C. for about 1 to 20 hours, to remove the protecting group(s), with the proviso that when the amine protected free acid is employed the reaction is carried out using a dehydrating agent such as dicyclohexylcarbodiimide.

The lactams of the compounds of general Formula I wherein each of $R_a$ and $R_b$ is hydrogen and $R_1$ is hydroxy are prepared from the corresponding amino acid ester of the structure

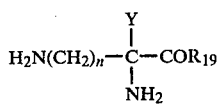

Formula VIII wherein n and Y have the meanings defined in Formula I, and $R_{19}$ is a straight or branched alkoxy group of from 1 to 8 carbon atoms, illustratively methoxy, ethoxy, isopropoxy, butoxy, or hexyloxy; by treating said amino acid esters with an appropriate base such as, sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures of these solvents for from ½ hour to 24 hours at a temperature of from about 0° to 120° C. optionally under a nitrogen atmosphere, with the additional step when Y is ClCH$_2$— of treatment with a chlorinating agent, such as, thionyl chloride, phosphorus oxychloride or phosphorus pentachloride in a solvent such as formamide dimethylformamide or dimethylacetamide for about 12 to 36 hours at a temperature of about 40° to 120° C.

The compounds of general Formula VIII are obtained by procedures generally known in the art from the corresponding amino acid, for example, by treating said amino acid with an appropriate alcohol, for example, methanol, ethanol, isopropyl alcohol, n-butanol or n-heptanol saturated with HCl gas.

The compounds of general Formula IX are obtained by the general method described in Synthesis 1973, 792, for example, by treating 1 equivalent of ornithine or lysine with 2 equivalents of benzoyl chloride then 2 equivalents of a base, such as, sodium hydroxide to form the bisamide which is treated with an acid anhydride, for example, acetic anhydride at about 90° C. for about ½ hour followed by treatment with aqueous formaldehyde and pyridine at about 25° C. for about 8 to 24 hours then treatment with water to give the oxodioxane which is treated with a catalytic amount of sodium methoxide in methanol then neutralized and treated with acid, for example, hydrochloric acid at about 120° C. for about 2 to 24 hours.

The individual optical isomers of the compounds of general Formula I wherein Z is R$_a$HN(CH$_2$)$_n$— wherein each of R$_a$ and R$_b$ is hydrogen and R$_1$ is hydroxy are obtained from the lactam of said compounds using a (+) or (−) binaphthylphosphoric acid salt by the method of R. Viterbo et al., Tetrahedron Letters 48, 4617 (1971). Other resolving agents such as (+) camphor-10-sulfonic acid may also be employed. Similarly the individual optical isomers of compounds of Formula I wherein Z is β-methylthioethyl, R is hydrogen and R$_1$ is hydroxy, are obtained from the free amino acid using a (+) or (−) binaphthylphosphoric acid salt or other agents such as (+) camphor-10-sulfonic acid.

The individual optical isomers of compounds of general Formula I wherein Z is γ-guanidinopropyl are obtained as described herein for the racemate only starting with the resolved ornithine analog.

The individual optical isomers of compounds of Formula I wherein Z is β-benzylthioethyl may be obtained as described herein for the racemate only starting with the resolved analog wherein Z is β-methylthioethyl. The individual optical isomers of compounds of Formula I wherein Z is β-thioethyl may be prepared from the resolved derivative wherein Z is β-benzylthioethyl, and the individual optical isomers of compounds of Formula I wherein Z is

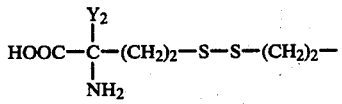

may be prepared from the resolved derivative wherein Z is β-thioethyl by procedures generally known in the art. The individual optical isomers of compounds of general Formula I wherein R is other than hydrogen and R$_1$ is other than hydroxy are obtained as described herein for the racemate only starting with the resolved free amino acid.

The compounds of general Formula III are prepared by coupling a 7-aminocephalosporanic acid or a derivative thereof having the formula

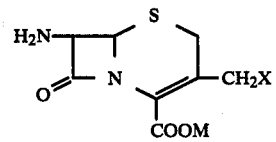

Formula IX wherein M is hydrogen or a negative charge and X is hydrogen or acetoxy, with an acid of the formula

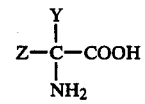

Formula X or a functional derivative thereof, such as, the acid chloride or an acid anhydride in the presence of a dehydrating agent such as dicyclohexylcarbodiimide when the free acid is employed wherein Z and Y have the meaning defined in general Formula I except Z is not

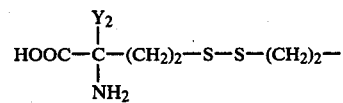

and the amino group is protected with a suitable blocking group, for example, tert-butoxycarbonyl followed by acid hydrolysis to remove the amino protecting groups.

The coupling reaction is generally carried out in a solvent, such as, ethyl acetate, dioxane, chloroform or tetrahydrofuran in the presence of a base, such as, alkaline bicarbonate. The temperature of the reaction may vary from about −10° to 100° C., and the reaction time may vary from about ½ hour to 10 hours. The cephalosporin products are isolated by conventional procedures. The compounds of Formula X are prepared by procedures described hereinabove, and the compounds of Formula IX are commercially available.

The following Example 1 illustrates the use of a compound of general Formula I wherein R$_1$ is hydroxy as a chemical intermediate in the preparation of a cephalosporin of Formula III.

EXAMPLE 1

7-[[2,5-Diamino-2-difluoromethylvaleryl]amino]-3-acetyloxymethyl-8-oxo-5-thia-1-azabicyclo[4.2.0]oct-2-ene-2-carboxylic acid A mixture of 1 g of 3-acetyloxy-7-amino-8-oxo-5-thia-1-azabicyclo[4.2.0]oct-2-ene-2-carboxylic acid and 1 g of 2,5-diamino-2-difluoromethylvaleric acid chloride wherein the free amino groups are protected with tert-butoxycarbonyl in 50 ml of ethylacetate is refluxed for 2 hours after which the solvent is removed leaving a residue which is treated with mild acid and chromatographed on silica gel using benzene-acetone as the eluant to give 7-[[2,5-diamino-2-difluoromethylvaleryl- ]amino]-3-acetyloxymethyl-8-oxo-5-thia-1-azabicyclo[4.2.0]oct-2-ene-2-carboxylic acid.

EXAMPLE 2

An illustrative composition for hard gelatin capsules is as follows:
(a) α,δ-diamino-α-difluoromethylvaleric acid: 20 mg
(b) talc: 5 mg
(c) lactose: 90 mg The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for an injectable suspension is the following 1 ml ampul for an intramuscular injection.

| | Weight per cent |
|---|---|
| (a) α-amino-α-difluoromethyl-γ-methylthiobutyric acid | 1.0 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 per ml of novel compound (a).

The following examples further illustrate the compounds of the invention.

EXAMPLE 4

α-Amino-α-difluoromethyl-γ-[S-(5'-desoxyadenosin-5'-yl)-thio]butyric acid

To a solution of the disodium salt of α-difluoromethyl-homocysteine (2 mmole) [prepared in situ from α-difluoromethylhomocystine (1 mmole) α-difluoromethylmethionine (2 mmole) or α-difluoromethyl-S-benzylmethionine (2 mmole) and sodium (2.1 mmole)] in liquid ammonia (100 ml) is added 5'-O-tosyladenosine (2 mmole). The reaction mixture is stirred for 2 hours and then the solvent is allowed to evaporate under a stream of nitrogen. The residue is dissolved in water (50 ml) and purified by passing first through an ion exchange resin column (KV-2 $NH_4^+$ form) and then a DEAE cellulose ($OH^-$ form) column. The aqueous eluate is evaporated under reduced pressure and crystallization of the residue from water ethanol yields pure α-amino-α-difluoromethyl-γ-[S-(5'-desoxyadenosin)5'-yl)thio]-butyric acid.

EXAMPLE 5

α-Amino-α-difluoromethyl-γ-[S-(5'-desoxyadenosin-5'-yl)-S-(methyl)thio]butyric acid To a solution of S-adenosyl-α-difluoromethyl-homocysteine (600 mg) in a mixture of acetic acid (4 ml) and formic acid (4 ml) is added methyl iodide (1 ml). The reaction mixture is kept under nitrogen in the dark for 8 days at room temperature. The solvent is removed under reduced pressure at room temperature and residue taken up in 0.1 N hydrochloric acid (8 ml). A saturated solution of Reinecke salt is added until the precipitation is complete. The precipitated salt (about 1 g) is treated with silver sulfate (1.5 g) in dry acetone at room temperature for 36 hours. The insoluble residue is filtered off and washed with methanol. The combined filtrates are concentrated under reduced pressure to yield α-amino-α-difluoromethyl-γ-[S-(5'-desoxyadenosin-5'-yl)-S-(methyl)-thio]butyric acid.

EXAMPLE 6

3-Amino-3-difluoromethyl-2-piperidone

To a solution of methyl-2-difluoromethyl-2,5-diaminopentanoate-dihydrochloride (2.7 g) in dry methanol (30 ml) is added under nitrogen 2 equivalents of sodium methylate in methanol (0.46 g of sodium in 20 ml of methanol). The reaction mixture is stirred for 3 hours at room temperature then the solvent is evaporated under reduced pressure. The residue is extracted with ether to yield crude 3-amino-3-difluoromethyl-2-piperidone which is purified either by crystallization from $CHCl_3$/pentane: (m.p.: 149° C.) or by distillation (b.p. 135° C./0.05 mmHg).

EXAMPLE 7

(−) and (+) 2-Amino-3-difluoromethyl-2-piperidone hydrochloride

To a solution of (−) binaphthylphosphoric acid (BNPA) (1.27 g) in hot ethanol (50 ml) is added a solution of (±) 3-amino-3-difluoromethyl-2-piperidone (0.546 mg) in hot ethanol (5 ml). On cooling, crystals separate. The reaction mixture is then let stand at 4° C. overnight. The precipitate is filtered off, washed with ethanol and diethyl ether to give 0.54 g of (−) binaphthylphosphoric salt ($[\alpha]_D = -409°$ C.=0.3, MeOH mp: 300° C.). Recrystallization of the mother liquor yields 0.15 g of (−) binaphthylphosphoric salt. Concentration of the filtrate gives 1.1 g of a sticky material which is treated with HCl 3 M at room temperature for 3 hours. The (−) BNPA is filtered off and the filtrate concentrated under reduced pressure. Recrystallization of the residue (320 mg) in ethanol affords (+) 3-amino-3-difluoromethyl-2-piperidonemonohydrochloride (160 mg) ($[\alpha]_D = +18°6$, C=1, MeOH) m.p. 238° C.). Treated in the same condition the (−) BNPA salt (436 mg) gives (−) 3-amino-3-difluoromethyl-2-piperidone monohydrochloride (137 mg) which is crystallized in ethanol (67 mg) ($[\alpha]_D = -19°$, C=1.02, MeOH; mp=240° C. dec.).

(−) and (+) 2-difluoromethyl-2,5-diamino pentanoic acid monohydrochloride (−) 3-Difluoromethyl-3-amino-2piperidone hydrochloride (60 mg) is heated in HCl 6 M (4 ml) at reflux for 12 hours. After concentration under reduced pressure, the residue is dissolved in water and the pH of the solution is adjusted to 4.5 with a solution of $NEt_3$. The solution is then concentrated under reduced pressure and the residue extracted many times with chloroform and then recrystallized from $H_2O$/EtOH to give (+) 2-difluoromethyl-2,5-diamino pentanoic acid monohydrochloride (54 mg) ($[\alpha]_D = +6°$, C=0,48; MeOH; mp≧240° C.). By an identical treatment, (+) 3-difluoromethyl-3-amino-2-piperidone hydrochloride (96 mg) gives (−) 2-difluoromethyl-2,5-diaminopentanoic acid monohydrochloride (56 mg) ($[\alpha]_D = -10°$, C=0.7 MeOH, mp≧244°).

EXAMPLE 8

2-Difluoromethyl-2-amino-5-guanidinopentanoic acid

To a solution of 2-difluoromethyl-2,5-diamino-pentanoic acid monohydrate monohydrochloride (5 g or 21.13 mmole) in NaOH 2M (8.5 ml) is added at once ethylthiouronium hydrobromide (7.82 g or 42.26 mmole). The pH of the solution is adjusted to 10.5 with NaOH 2M and maintained to that value for 4 days. The reaction mixture is then neutralized to pH=7 with 1 M HCl and concentrated under reduced pressure. The residue is passed on an Amberlite IR 120 H+ form column. Elution with NH$_4$OH 2 M affords 2-difluoromethyl-2-amino-5-guanidinopentanoic acid which is recrystallized from H$_2$O/EtOH (2.3 g) m.p. 257° C.

EXAMPLE 9

Methyl-2-difluoromethyl-2,6-dibenzaldimine hexanoate

To a solution of lithium diisopropylamide (60 mmole prepared in situ in tetrahydrofuran, cooled to −78° C., magnetically stirred and kept under nitrogen, is added slowly a solution of methyl-2,6-dibenzaldimine hexanoate (16.82 g or 50 mmole) in dry THF (60 ml). The reaction mixture is allowed to rise to room temperature over a period of 2 hours and is then rapidly warmed up to 40° C. The nitrogen inlet is replaced by a balloon filled with ClCHF$_2$ (1 l). The reaction mixture is kept overnight at room temperature under stirring and then is hydrolyzed with water. Usual ether extraction yields methyl-2-difluoromethyl-2,6-dibenzylideneamino hexanoate.

EXAMPLE 10

Methyl-2-difluoromethyl-2,6-diaminohexanoate dihydrochloride

A solution of methyl-2-difluoromethyl-2,6-dibenzaldimine hexanoate (15.4 g or 40 mmole) in ether (20 ml) is magnetically stirred with 2 N hydrochloric acid (110 ml) for 1 hour. Usual ether extraction and evaporation to dryness of the aqueous phase affords methyl-2-difluoromethyl-2,6-diamino hexanoate dihydrochloride (9.15 g 85%) which is crystallized from methanol, ether, m.p. 207° C.

EXAMPLE 11

2-Difluoromethyl-2,6-diaminohexanoic acid hydrochloride

A solution of methyl-2-difluoromethyl-2,6-diaminohexanoate dihydrochloride (4 g, 14 mmole) in concentrated HCl is treated under reflux for 20 hours. After evaporation to dryness and decoloration with charcoal, the pale solid obtained is dissolved in absolute ethanol. The pH of the solution is adjusted to 4.5 with a solution of triethylamine (M) in absolute ethanol upon which the α-difluoromethyl-lysine monohydrochloride precipitated. Recrystallization from water/ethanol yields analytically pure α-difluoromethyl lysine hydrochloride as white crystals, m.p.>260° C. (dec.).

EXAMPLE 12

2-Difluoromethyl-2,5-diaminopentanoic acid

Under nitrogen a solution (500 ml) of 2 M butyl lithium in hexane is added to a stirred solution of 143.1 ml of diisopropylamine in 1.5 liters of tetrahydrofuran at −78° C. after which 261 g (0.81 mole) of ornithine dibenzaldimine methyl ester in 1.5 liters of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l) for 3 hours, the mixture extracted several times with chloroform and the aqueous solution evaporated to dryness. The oily residue is refluxed with 12 N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7–8 liters of acetone. The precipitated product is filtered off and washed with ethanol. The crude product is recrystallized by dissolving in about 150 ml hot water and treatment of the solution with hot ethanol (450 ml). On cooling crystals of 2-difluoromethyl-2,5-diaminopentanoic acid hydrochloride monohydrate separate 71 g (37%), m.p. 183° C.

EXAMPLE 13

3-Hydroxymethyl-3-amino-2-piperidone

2-Hydroxymethyl-2,5-diaminopentanoic acid hydrochloride (5 g or $2.5 \times 10^{-2}$ mole) is suspended in 75 ml of absolute methanol and the solution is saturated with dry hydrogen chloride. The homogenous solution is then heated under reflux for 48 hours. The reaction mixture is regularly saturated with dry hydrogen chloride. The solvent is evaporated under reduced pressure and the hygroscopic residue is dried under high vacuo (6.2 g) and identified as dihydrochloride of 2-hydroxymethyl-2,5-diaminopentanoic acid methyl ester by NMR. The ester (6.2 g) is dissolved in 100 ml of absolute methanol and 175 ml of a methanolic solution of sodium methylate (1.15 g of Na or $5 \times 10^{-2}$ mole) is added. The reaction mixture is stirred at room temperature under nitrogen for 24 hours. The solvent is evaporated under reduced pressure and the residue is extracted many times with hot chloroform to yield analytically pure 3-hydroxymethyl-3-amino-2-piperidone (2.9 g) (yield 81%), m.p. 145° C.

EXAMPLE 14

2-Amino-5-benzyloxycarbonylaminopentanoic acid

A solution of 2,5-diaminopentanoic acid monohydrochloride (16.9 g) and copper carbonate (30 g) in 750 ml of water is heated at reflux temperature for 4 hours. The insoluble material is filtered off and washed with hot water. The filtrate is allowed to cool to room temperature then sodium bicarbonate (30 g) is added followed by the addition of a solution of benzylchloroformate (25.6 g) in 750 ml of acetone. The reaction mixture is stirred overnight. The precipitate is filtered off, washed with water and then resuspended in hot water (300 ml). Hydrogen sulfide gas is bubbled in the solution for 2 hours. The solution is then acidified with concentrated hydrochloric acid (7.5 ml) and the black precipitate filtered off. The pH of the filtrate is adjusted to 6 whereupon 2-amino-5-benzyloxycarbonylaminopentanoic acid precipitates and is collected.

EXAMPLE 15

α-Difluoromethylhomocystine

Air is bubbled into a solution of α-difluoromethylhomocysteine (9.25 g or 0.05 M) in 100 ml of water containing a few drops of 1% aqueous ferric chloride for several hours. The crude α-difluoromethylhomocystine which precipitates is filtered off and then redissolved in water by addition of concentrated hydrochloric acid. Neutralization of the solution by dropwise addition of concentrated ammonia to a pH of about 4 precipitates α-difluoromethylhomocystine.

EXAMPLE 16

α-Difluoromethyl-S-benzylhomocysteine

A mixture of α-difluoromethylmethionine (0.2 mole), concentrated hydrochloric acid (0.2 l) and benzylchloride (23 ml) is heated to reflux temperature for 24 hours. The reaction mixture is then concentrated under reduced pressure to a syrup which is dissolved in water. The aqueous solution is extracted with ether, and the aqueous phase is heated with charcoal and filtered. The precipitate is diluted with hot water to a volume of 100 ml and brought to a pH of about 4–5 by addition of aqueous ammonia. On cooling, α-difluoromethyl-S-benzylhomocysteine precipitates and is collected.

EXAMPLE 17

S-Tritylhomocysteine

To a solution of anhydrous homocysteine hydrochloride (0.1 mole) in 60 ml of dimethylformamide is added 42 g (0.15 mole) of tritylchloride. The reaction mixture is stirred at room temperature for 2 days. Upon addition of 10% sodium acetate solution (500 ml) S-tritylhomocysteine precipitates together with triphenylcarbinol. Recrystallization in acetone affords pure S-tritylhomocysteine.

EXAMPLE 18

S-Benzyloxycarbonylhomocysteine

To an ice cooled solution of L-cysteine hydrochloride (0.1 mole) in 1 molar aqueous sodium carbonate (200 ml) covered with ether (100 ml) is added benzylchloroformate (0.095 mole) in one portion with vigorous stirring. After 1 hour at 0° C. the temperature is allowed to rise to 10° C. and maintained at that temperature for 1 hour. The precipitate is filtered off, washed with water then with acetone and recrystallized from acetic acid to give S-benzyloxycarbonylhomocysteine.

EXAMPLE 19

5-Acetylamino-2-benzyloxycarbonylamino-2-difluoromethylpentanoic acid

To a solution of 1.82 g (0.01 mole) of 5-acetylamino-2-amino-2-difluoromethylpentanoic acid in 22 ml of 1 molar sodium hydroxide is added a solution of 2 g (0.18 mole) of benzylchloroformate in 10 ml of acetone. The reaction mixture is stirred at room temperature for 2 hours and then is carefully neutralized to a pH of 7 using hydrochloric acid whereupon 5-acetylamino-2-benzyloxycarbonylamino-2-difluoromethylpentanoic acid precipitates and is collected.

EXAMPLE 20

2-Amino-5-acetylamino-2-difluoromethyl-1-oxopentaneaminoacetic acid

To a solution of 0.25 g (1 mM) of 5-acetylamino-2-benzyloxycarbonylamino-2-difluoromethylpentanoic acid methyl ester in 4 ml of dioxane is added 0.18 g of benzylglycinate and 0.21 g of dicyclohexylcarbodiimide. The reaction mixture is stirred for 12 hours at room temperature then extracted with ethyl acetate. The aqueous phase is washed with a 10% solution of bicarbonate then water and dried over magnesium sulfate. Evaporation of the solvent affords an oily residue which is dissolved in glacial acetic acid (5 ml). The solution is then hydrogenated over Pd/C 10% (30 mg). After stirring the reaction mixture for 12 hours at room temperature the catalyst is filtered off. The filtrate is diluted with toluene and then concentrated under reduced pressure. The residue is purified by ion exchange chromatography on an Amberlite IR 120 active column to give 2-amino-5-acetylamino-2-difluoromethyl-1-oxopentaneaminoacetic acid.

EXAMPLE 21

2-Acetylamino-5-(2-aminopropionylamino)-2-difluoromethylpentanoic acid

To a solution of 0.5 g of 2-acetylamino-5-benzyloxycarbonylamino-2-difluoromethylpentanoic acid in 4 ml of dimethylformamide is added 0.27 g of benzylbromide and 0.4 ml of dicyclohexylamine. The reaction mixture is stirred for 12 hours and then the precipitate is filtered off. The filtrate is evaporated under reduced pressure, and the residue is partitioned between ethylacetate and water. The organic phase is washed with aqueous hydrochloric acid, water, 5% sodium bicarbonate, water and brine then dried over magnesium sulfate. The solvent is evaporated and the residue heated in 5 ml of trifluoroacetic acid for 1 hour at room temperature. The excess trifluoroacetic acid is then stripped off under reduced pressure. The residue is suspended in 5 ml of ether and a solution of N-benzyloxycarbonyl-O-ethoxycarbonylalanine (0.4 g) and triethylamine (0.2 g) in 5 ml of ether is added. Stirring is continued overnight at room temperature. The solvent is evaporated. The resulting syrupy residue is dissolved in glacial acetic acid, and the solution hydrogenated over Pd/C 10% (30 mg) for 12 hours. The catalyst is then filtered off. The filtrate is concentrated and the residue is purified by ion exchange chromatography on an Amberlite IR 120 acidic column to give 2-acetylamino-5-(2-aminopropionylamino)-2-difluoromethylpentanoic acid.

EXAMPLE 22

2-Acetylamino-5-amino-2-difluoromethyl-1-oxopentaneaminoacetic acid

A solution of 0.25 g of 2-acetylamino-5-benzyloxycarbonylamino-2-difluoromethylpentanoic acid in 4 ml of dioxane is treated at 0° C. with 0.11 g of ethylchloroformate and 0.1 g of triethylamine. The reaction mixture is stirred at 0° C. for 1 hour after which 0.18 g of benzylglycinate is added. The reaction mixture is stirred for an additional 12 hours then extracted with ethylacetate. The organic phase is washed with a solution of bicarbonate, then water and dried over magnesium sulfate. Evaporation of the solvent gives an oily residue which is dissolved in glacial acetic acid (5 ml). The solution is then hydrogenated over Pd/C 10% (30 mg). After stirring the reaction mixture for 12 hours the catalyst is filtered off. The filtrate is diluted with toluene and concentrated under reduced pressure. The residue is purified by ion exchange chromatography on an Amberlite IR 120 acidic column to give 2-acetylamino-5-amino-2-difluoromethyl-1-oxopentaneaminoacetic acid.

EXAMPLE 23

5-Acetylamino-2-difluoromethyl-2-propionylaminopentanoic acid methylester

To a solution of 0.47 g of 5-acetylamino-2-amino-2-difluoromethylpentanoic acid methylester in 10 ml of ether is added simultaneously at 0° C. 0.18 g of propionylchloride and 0.2 g of triethylamine. The reaction mixture is stirred at room temperature for 2 hours then extracted with ethylacetate. The organic phase is washed with a solution of sodium bicarbonate, water, then brine and dried over magnesium sulfate. Evaporation of the solvent gives 5-acetylamino-2-difluoromethyl-2-propionylaminopentanoic acid methylester.

EXAMPLE 24

2-Acetylamino-2-difluoromethyl-5-guanidinopentanoic acid

To a solution of 2-acetylamino-5-amino-2-difluoromethylpentanoic acid (0.45 g) in 4 ml of 0.5 M aqueous sodium hydroxide is added 1.8 g of ethylthiouroniumhydrobromide. the pH of the solution is adjusted to 9 with a solution of sodium hydroxide and maintained at that pH for 24 hours. The reaction mixture is then neutralized to a pH of 7 with hydrochloric acid and 2-acetylamino-2-difluoromethyl-5-guanidinopentanoic acid is isolated by ion exchange chromatography on an Amberlite IR 120 resin.

EXAMPLE 25

2-Amino-5-benzyloxycarbonylamino-2-difluoromethylpentanoic acid

To a solution of the copper salt of 2-difluoromethyl-2,5-diaminopentanoic acid in water, prepared by reacting 2-difluoromethyl-2,5-diaminopentanoic acid monohydrate hydrochloride (2.4 g) with copper carbonate (6 g), is added slowly at 0° C. with stirring 1.1 g of benzylchloroformate. The reaction mixture is stirred for an additional 3 hours at room temperature after which hydrogen sulfide is passed through the solution until it becomes colorless. The precipitate is filtered off, and the pH of the aqueous solution is adjusted to 6 by the addition of hydrochloric acid. Upon concentration 2-amino-5-benzyloxycarbonylamino-2-difluoromethylpentanoic acid is obtained.

By the above procedure only using tert-butoxycarbonylazide, acetylchloride or benzoylchloride in place of benzylchloroformate gives respectively 2-amino-5-tert-butoxycarbonylamino-2-difluoromethylpentanoic acid, 5-acetylamino-2-amino-2-difluoromethylpentanoic acid and 2-amino-5-benzyloxycarbonylamino-2-difluoromethylpentanoic acid.

EXAMPLE 26

2-Acetylamino-5-amino-2-difluoromethylpentanoic acid

To a solution of 2.9 g of 2-amino-5-tert-butoxycarbonylamino-2-difluoromethylpentanoic acid in 10.5 ml of 1 M sodium hydroxide is added at 0° C. simultaneously 0.19 g of acetylchloride and 5 ml of 2 M aqueous sodium hydroxide. The reaction mixture is stirred for 3 hours at room temperature. The alkaline aqueous solution is then adjusted to a pH of 2 with hydrochloric acid and extracted with ethylacetate. After usual work-up the solvent is evaporated and the residue taken up in trifluoroacetic acid. After concentration and purification by ion exchange chromatography on a resin 5-amino-2-acetylamino-2-difluoromethylpentanoic acid is obtained.

EXAMPLE 27

5-Amino-2-difluoromethyl-2-(2-aminopropionylamino)-pentanoic acid

To a solution of 3.2 g of 2-amino-5-benzyloxycarbonylamino-2-difluoromethylpentanoic acid in 10 ml of 1 M aqueous sodium hydroxide is added at 0° C. simultaneously a solution of tert-butoxycarbonylazide, prepared from 3 g of tert-butoxycarbonylhydrazine, and a solution of 5.5 ml of 2 M aqueous sodium hydroxide. The reaction mixture is stirred overnight then extracted twice with 50 ml of ether. The alkaline aqueous solution is then adjusted to a pH of 2 with hydrochloric acid and extracted with ethylacetate. Usual work-up gives a solid residue which is dissolved in 15 ml of dry dimethylformamide and treated at room temperature with 1.7 g of benzylbromide in the presence of 2 ml of dicyclohexylamine. The reaction mixture is stirred for 14 hours and then the precipitate is filtered off. The filtrate is evaporated under reduced pressure. The resulting residue is partitioned between 100 ml of ethylacetate and water. The organic phase is washed successively with 20 ml of 1 normal aqueous hydrochloric acid, 20 ml of water, 20 ml of 5% aqueous sodium bicarbonate, 20 ml of water and 50 ml of brine then dried over magnesium sulfate. The solvent is evaporated and the residue taken up in 10 ml of trifluoroacetic acid. After 1 hour at room temperature the excess trifluoroacetic acid is stripped off under reduced pressure and the residue is taken up in a saturated solution of sodium bicarbonate and extracted with 50 ml of ether. The ether phase is dried over magnesium sulfate and then added at 0° C. to a solution of N-benzyloxycarbonyl-O-ethoxycarbonylalanine (2 g) in 20 ml of ether. Stirring is continued overnight at room temperature. The solvent is evaporated and the resulting syrupy residue is taken up in glacial acetic acid (20 ml) and hydrogenated over Pd/C 10% (200 mg). After completion of the hydrogen uptake the catalyst is filtered off. The filtrate is concentrated under reduced pressure with toluene and the residue purified by ion exchange chromatography on an acidic resin to give 5-amino-2-(2-aminopropionylamino)-2-difluoromethylpentanoic acid.

EXAMPLE 28

2-[(2,5-Diamino-2-difluoromethyl-1-oxopentane)amino]-propionic acid

To a solution of 2,5-diamino-2-difluoromethylpentanoic acid monohydrate hydrochloride (2.35 g) in 10 ml of 2 M aqueous sodium hydroxide is added at 0° C. simultaneously a solution of 10 ml of 2 molar aqueous sodium hydroxide and a solution of tert-butoxycarbonylazide prepared from 3 g of tert-butoxycarbonylhydrazine. The reaction mixture is stirred overnight at room temperature and then extracted twice with 250 ml portions of ether. The alkaline aqueous solution is adjusted to a pH of 2 with hydrochloric acid and extracted with ethylacetate. After usual work-up the solvent is evaporated and the residue taken up in 40 ml of dry ether. After addition of 1 g of triethylamine an ether solution of 1 g of ethylchloroformate is added slowly at 0° C. with stirring. The precipitate is filtered off and the ether solution is added at once to a solution of alanine tert-butylester (1.5 g). Stirring is continued overnight and the solvent is evaporated. The residue is taken up in trifluoroacetic acid. After concentration and purification by ion exchange chromatography on an Amberlite IR 120 resin 2-[(2,5-diamino-2-difluoromethyl-1-oxopentane)amino]propionic acid is obtained.

We claim:

1. A compound having the formula

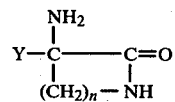

wherein Y is $F_2CH-$, $F_3C$ or $Cl_2CH-$; and n is the integer 3 or 4.

2. A compound according to claim 1 wherein n is the integer 3.

3. A compound according to claim 1 wherein n is the integer 4.

4. A compound according to claim 2 wherein Y is $F_2CH-$.